United States Patent
Dong (10) Patent No.: US 7,929,744 B2
(45) Date of Patent: Apr. 19, 2011

(54) METHOD AND DEVICE FOR COLOR BLOOD FLOW FRAME AVERAGING

(75) Inventor: Yongqiang Dong, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 841 days.

(21) Appl. No.: 11/927,299

(22) Filed: Oct. 29, 2007

(65) Prior Publication Data

US 2008/0298651 A1 Dec. 4, 2008

(30) Foreign Application Priority Data

Jun. 1, 2007 (CN) .......................... 2007 1 0112301

(51) Int. Cl.
*G06K 9/00* (2006.01)
*A61B 8/00* (2006.01)
(52) U.S. Cl. .................. 382/128; 382/165; 600/454
(58) Field of Classification Search .................. 382/100, 382/128, 129, 130, 131, 132, 133, 134, 162, 382/165, 168, 172, 173, 181, 199, 274, 275, 382/276, 286, 305, 312; 600/454, 443, 462, 600/221, 458; 378/52; 351/221
See application file for complete search history.

(56) References Cited

U.S. PATENT DOCUMENTS

| | | | |
|---|---|---|---|
| 6,419,632 B1 * | 7/2002 | Shiki et al. ..................... | 600/443 |
| 6,599,248 B1 * | 7/2003 | Tamura .......................... | 600/454 |
| 6,913,662 B2 * | 7/2005 | Barilovits et al. | |
| 7,022,079 B2 * | 4/2006 | Ogasawara .................... | 600/458 |
| 7,044,913 B2 * | 5/2006 | Shiki .............................. | 600/454 |
| 7,404,640 B2 * | 7/2008 | Ferguson et al. ............. | 351/221 |
| 7,803,116 B2 * | 9/2010 | Sikdar et al. .................. | 600/462 |
| 7,874,988 B2 * | 1/2011 | Shiki ............................. | 600/443 |
| 2005/0124886 A1 * | 6/2005 | O'Donnell et al. | |
| 2008/0298651 A1 * | 12/2008 | Dong ............................ | 382/128 |

FOREIGN PATENT DOCUMENTS

| | | | |
|---|---|---|---|
| CN | 1867295 | * | 11/2006 |
| JP | 2005312632 | * | 11/2005 |

OTHER PUBLICATIONS

China patent application No. 200710112301.3, Search Report dated Jul. 16, 2007.

* cited by examiner

*Primary Examiner* — Seyed Azarian
(74) *Attorney, Agent, or Firm* — Kory D. Christenser; Stoel Rives LLP (57) ABSTRACT

The present invention provides a method and device for color blood flow frame averaging. In the present invention, whether aliasing occurs to an output blood flow velocity of a previous frame is first determined. If aliasing does occur to the output blood flow velocity of the previous frame, the output blood flow velocity of the previous frame will be moved, and the moved output blood flow velocity of the previous frame is then subjected to the frame averaging. The present invention can improve and eliminate the "shadow" in the output blood flow velocity of the current frame due to velocity aliasing of the previous frame existing in the prior color frame averaging processing, such that the blood flow velocity appears more natural and has a more reasonable distribution.

15 Claims, 7 Drawing Sheets

METHOD AND DEVICE FOR COLOR BLOOD FLOW FRAME AVERAGING

STATEMENT OF RELATED APPLICATION

The present application claims the priority of the Chinese Patent Application No. 200710112301.3, entitled "Method and Device for Color Blood Flow Frame Averaging", filed on Jun. 1, 2007, which is incorporated herein by reference.

FIELD OF THE INVENTION

The present invention relates to the field of ultrasound imaging, and more particularly, to a method and device for color blood flow frame averaging for use in an ultrasound imaging system.

BACKGROUND OF THE INVENTION

Figure 1:
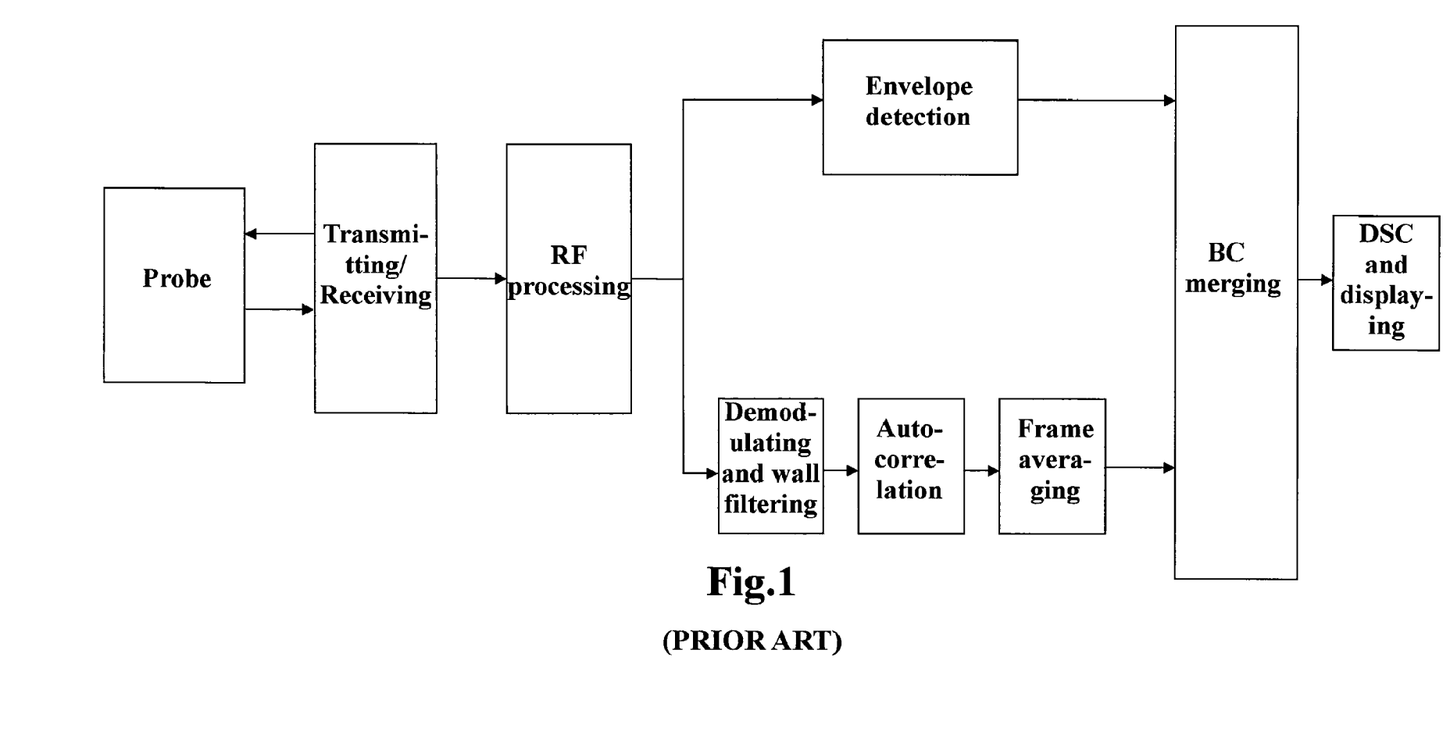
FIG. 1 is a schematic block diagram of a color ultrasound imaging.

The color blood flow imaging technology, the most extraordinary and important function of a commercial color ultrasonic apparatus, is used to measure the presence of a blood flow in the human body and estimate the kinetic parameters of the blood flow in the human body. A schematic block diagram of the commercial color ultrasonic apparatus is shown in FIG. 1. A pulse signal transmitted from the probe enters the human body and, having been reflected by the human body tissue, the blood flow and the moving organs, is received by an ultrasound probe, and finally gets amplified, analog-to-digital converted and beamformed by an RF processing circuit to form a radio frequency (RF) signal. The RF signal may form a black and white image of the human body tissue through an envelope detection channel or may form a color image regarding the human body blood flow motion parameters through a color blood flow processing channel. The image is then sent to the display for displaying having gone through a merge of an anatomic image B and a color flow image C, a coordinate transformation, an image post-processing, etc., as shown in FIG. 1. These processes may be in different orders, or alternatively include additional image post-processing steps.

There is a key step going on in the color blood flow processing channel, i.e., a color frame averaging step, also known as color image time averaging processing. The object of this processing is to increase the signal-to-noise ratio (SNR) by time accumulation, so as to improve the sensitivity of the commercial ultrasonic apparatus in detection of a weak blood flow signal.

Color frame averaging processing technologies have been described in some public literatures and patents. Franklin [1] et al. of ATL proposed a color frame averaging method in 1993. This color frame averaging technology uses a first-order IIR filter for the frame averaging between consecutive color velocity frames. When the velocity increases, the velocity after the frame averaging is increased therewith swiftly; and when the velocity declines, the velocity after the frame averaging is decreased slowly. Thus, even during the end diastole, the color velocity can be maintained for a period of time to improve the color sensitivity. However, this patent does not take into account the possibility that there may be two consecutive frames, the directions of which are reverse. The color velocity frame averaging as described in document [1] is referred to as scheme I and described as follows. If the input blood flow velocity of the current frame is larger than the output blood flow velocity of the previous frame, the input blood flow velocity of the current frame is outputted as the output blood flow velocity of the current frame. Otherwise, the output blood flow velocity of the previous frame and the input blood flow velocity of the current frame are frame-averaged, i.e., $V_{out}(n)=\alpha V_{out}(n-1)+(1-\alpha)V_{in}(n)$, where, $\alpha$ is the frame averaging coefficient, $V_{in}(n)$ refers to the input blood flow velocity of the current frame, $V_{out}(n)$ and $V_{out}(n-1)$ refer to respectively the current frame velocity and the previous frame velocity outputted by the color frame averaging.

Collaris et al. [2] described a time averaging scheme using a so-called "persistence filter". This scheme also makes use of the IIR filter and moreover takes the possibility of opposing blood flow velocities into account. When the blood flow velocity of the current frame is in a different direction than that of the previous frame, or when the blood flow velocity value of the current frame is larger than that of the previous frame, the velocity direction of the current frame is used, and the blood flow velocity value of the current frame outputted by the color frame averaging processing is independent of the blood flow velocity value of the previous frame. Otherwise, a first-order IIR recursive filter is used to maintain the color blood flow velocity for a period of time. In contrast to scheme I, the scheme in [2], hereinafter referred to as scheme II, further considers the change in the directions of the blood flows between consecutive velocity frames. This is how scheme II is implemented: if the input blood flow velocity of the current frame is larger than the output blood flow velocity of the previous frame, or when the direction of the input blood flow of the current frame is opposite to that of the output blood flow of the previous frame, the input blood flow velocity of the current frame is outputted as the output blood flow velocity of the current frame. Otherwise, the output blood flow velocity of the previous frame and the input blood flow velocity of the current frame are frame-averaged, i.e., $V_{out}(n)=\alpha V_{out}(n-1)+(1-\alpha)V_{in}(n)$, where $\alpha$, $V_{in}(n)$, $V_{out}(n)$ and $V_{out}(n-1)$ have the same meanings as in scheme I.

In the literatures and patents published later on, some extensions are made to scheme II. To increase the pulsation of the blood flow, Forestieri [3] and Smith [4] adjust the magnitude of the frame averaging coefficient based on the calculated blood flow velocities of the current frame and the previous frame. Unfortunately, the final frame averaging algorithm does not take velocity aliasing into account. Likewise, Wong [5] of Siemens merely introduces two more parameters on the basis of scheme II, i.e., energy threshold and velocity threshold, to identify some irregularities occurring during the blood flow velocity calculation. Wong [5] of Siemens still disregards the effect of the blood flow velocity aliasing upon the velocity frame averaging.

All of these improved frame averaging techniques make no substantial changes to scheme II, though they consider the change in the directions of the blood flows between consecutive velocity frames. Moreover, a so-called "shadow" phenomenon always occurs in the clinical diagnosis of these schemes.

As apparent, the disadvantage of the existing color velocity frame averaging techniques is that when two consecutive frames have blood flows of opposing directions, the current blood flow frame is output directly without taking into account the relationship between the previous frame velocity value and the current frame velocity value if the velocity aliasing occurs. This operation of directly dropping the previous frame velocity value is a nonlinear processing, causing a "shadow" in the blood flow velocity diagram of the subsequent frame, which continues to appear in the following frames.

The cause for the presence of "shadow" is described as follows.

Figure 2:
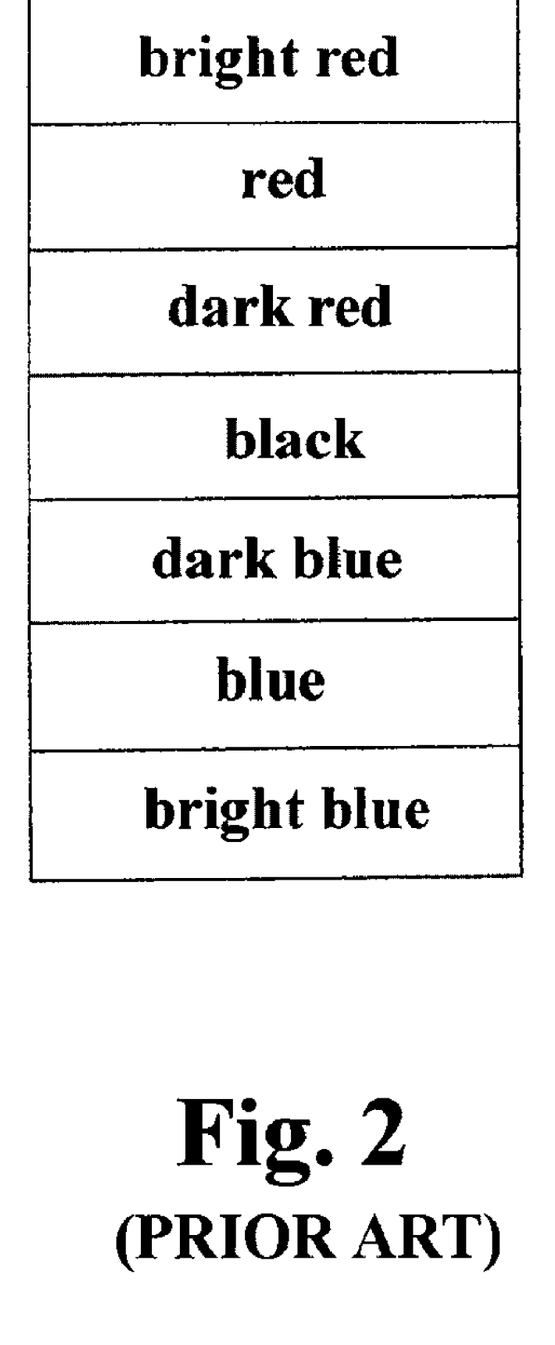
FIG. 2 shows a schematic format of a common color scale indication bar.

It is assumed that color scale indication bars are used to indicate the color blood flow velocity as shown in FIG. 2. The color red indicates a blood flow velocity in the direction towards the probe. As the velocity increases, the color scale exhibits black, dark red, red and bright red successively. The color blue denotes a blood flow velocity in the direction away from the probe. As the departure velocity increases, the color scale exhibits black, dark blue, blue and bright blue successively.

Figure 3:
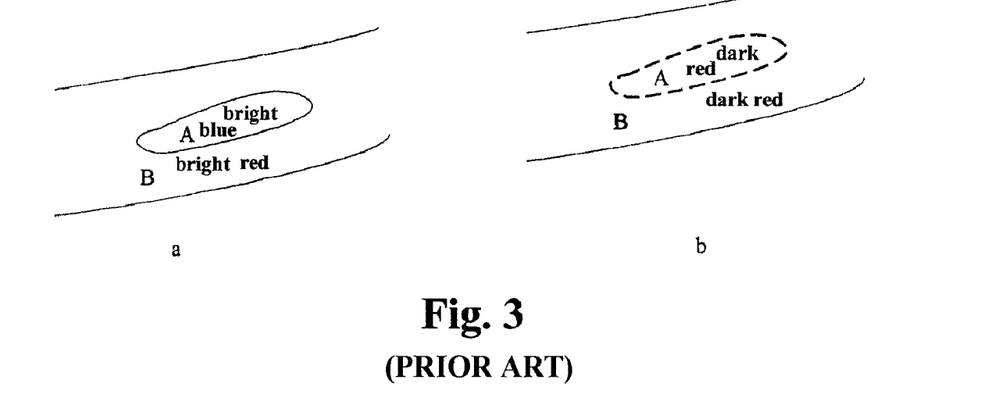

FIG. 3 shows two blood flow velocity diagrams, taking the carotid as an example, in which, FIG. 3a shows the blood flow velocity diagram of the previous frame having been subjected to frame averaging, and FIG. 3b shows the blood flow velocity diagram of the current frame under an auto-correlation estimation. The changes in velocity with time as characterized in these two diagrams are consistent with the actual changes of the blood flow velocity in the carotid. It can be seen from FIG. 3a that it is during the systole of the cardiac cycle that the blood flow velocity of the carotid is being scanned. Therefore, the carotid has a maximum blood flow velocity in the whole cardiac cycle. At this time, the blood flow velocity appears bright blue in the middle of the blood vessel, as indicated in area A in FIG. 3a. In other spatial areas of the blood vessel, such as area B shown in FIG. 3a, the blood flow is at a slightly lower speed than the blood flow in the middle of the blood vessel, i.e., the velocity in area B in FIG. 3a is slightly lower than that in area A, and the blood flow velocity in area B exhibits bright red. In the subsequent frame of the blood flow, as the blood flow velocity scanned at this moment is not the maximum blood flow velocity in the whole cardiac cycle, the blood flow velocity in the entire blood vessel exhibits dark red (or red), as shown in FIG. 3b. Both area A and area B in FIG. 3a exhibit dark red at this time.

Figure 4:
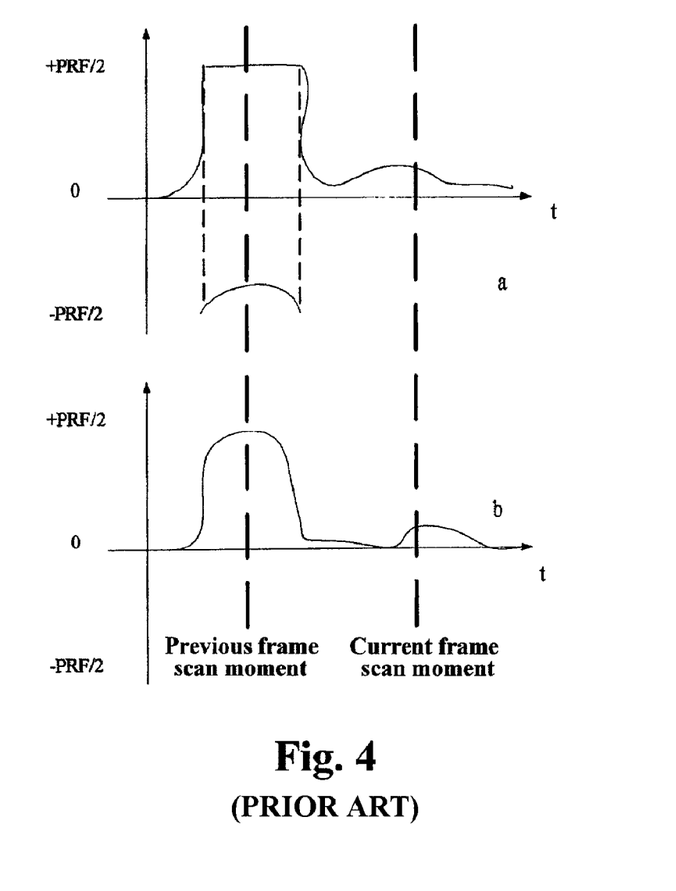

FIG. 4 shows changes of the blood flow velocity with time in area A and area B during scanning two consecutive frames, in which PRF refers to a pulse repetition frequency. FIG. 4a shows the changes in the blood flow velocity with time in area A. During scanning the previous frame, the blood flow velocity in area A is just within the systole, when aliasing occurs to the blood flow velocity in area A, exhibiting bright blue. The blood flow velocity in area B is also within the systole, but the blood flow velocity is slightly lower than that in the middle of the blood vessel, thus exhibiting bright red. When scanning the current frame, as indicated by the vertical heavy dotted line on the right-hand side of FIG. 4, since the blood flow velocity being scanned does not correspond to the maximum blood flow velocity, neither the blood flow velocity in area A nor the blood flow velocity in area B is large, exhibiting dark red in the image.

Figure 5:
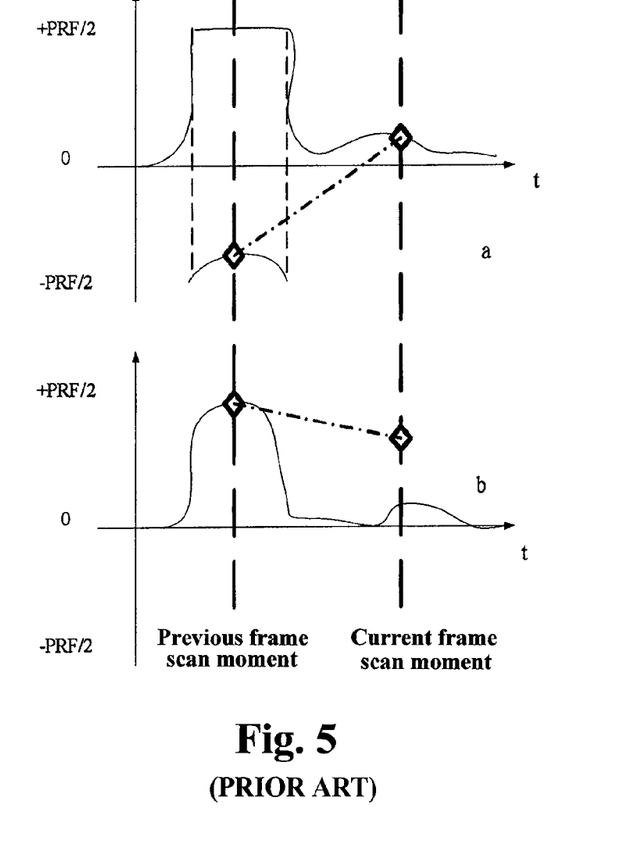
Figure 6:
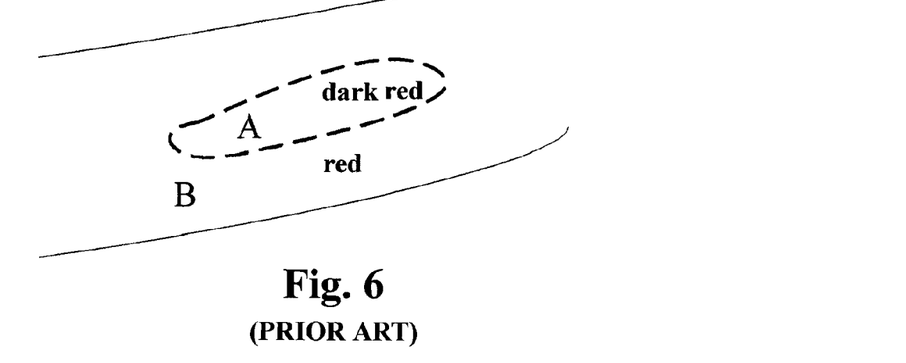
FIG. 6 shows a color blood flow velocity resultant from using an existing color frame averaging technology.

According to the existing color frame averaging technology described in scheme II, in area A, since the blood flow velocity of the previous frame is bright blue, but the blood flow velocity of the current frame is dark red, the blood flow velocities have opposing directions. According to the frame averaging described as scheme II, it is the velocity of the current velocity frame that should be outputted, i.e., dark red. However, in area B, because the blood flow velocity of the previous frame and that of the current frame have the same direction, and meanwhile the blood flow velocity of the previous frame is larger than that of the current frame, according to scheme II, the output color blood flow velocity of the current frame is obtained by the recursion of the output blood flow velocity of the previous frame onto the input blood flow velocity of the current frame. Therefore, the blood flow velocity at this time is red instead of dark red. The flow of the frame averaging may be seen from the diamonds indicating velocities as shown in FIG. 5. The dot-and-dash lines in FIG. 5a and 5b each indicate the changes in the blood flows of the previous frame and the current frame after being processed by the existing color frame averaging technology. It can be seen from FIG. 5 that in area A, the output blood flow velocity of the current frame remains dark red, while in area B, the color of the output blood flow velocity of the current frame is lightened by the bright red color of the output blood flow velocity of the previous frame, thus exhibiting red. Thus, the prior art will result in a color blood flow velocity diagram shown in FIG. 6, in which the blood flow velocity in the middle of the blood vessel appears dark red, and appears red in both sides of the blood vessel. As a result, a dark red block stands amidst a red blood flow. This block of blood flow having a different color is referred to as a "shadow". This phenomenon does not make sense in clinics. In a clinical blood flow velocity diagram, it should be that the blood flow velocity is high in the middle of the blood vessel, and the blood flow velocity at the proximity of the vessel wall is relatively lower. Furthermore, the larger the frame averaging coefficient, the greater the difference between the blood flow velocities in the middle of the blood vessel and in the proximity of the vessel wall; the greater the difference between the blood flow velocities of the current frame and of the previous frame, the greater the difference between the blood flow velocities in the middle of the blood vessel and in the proximity of the vessel wall. The same applies to the reverse blood flow. That is, the prior art would output a blood flow velocity diagram in which a dark blue block appears amidst a blue blood flow. Particularly, an obvious line trail will appear along the edges of area A and area B, i.e., the edge intersecting the dark red area and the red area, or the edge intersecting the dark blue area and the blue area.

These "shadows" and line trails are unfavorable in the color blood flow image. Therefore, there exists a need to provide a method and device that alleviates or eliminates these "shadows" and line trails concerning blood flow velocities.

SUMMARY OF THE INVENTION

The present invention provides a method for color blood flow frame averaging. The method comprises: acquiring an input blood flow velocity of the current frame and an output blood flow velocity of the previous frame; determining whether the input blood flow velocity of the current frame is in an opposite direction to that of the output blood flow velocity of the previous frame; determining whether aliasing occurs to the output blood flow velocity of the previous frame if the input blood flow velocity of the current frame is in an opposite direction to that of the output blood flow velocity of the previous frame; and processing the input blood flow velocity of the current frame and the output blood flow velocity of the previous frame to obtain an output blood flow velocity of the current frame if aliasing occurs to the output blood flow velocity of the previous frame.

The step of determining whether aliasing occurs further comprises: comparing parameters regarding the previous frame with corresponding first threshold values, and if the parameters regarding the previous frame are larger than the corresponding first threshold values, determining occurrence of aliasing to the output blood flow velocity of the previous frame. The parameters regarding the previous frame comprise any one of or any combination of: a blood flow velocity of the previous frame, blood flow energy of the previous frame, a blood flow variance of the previous frame, and an absolute value of a difference between the output blood flow velocity of the previous frame and the input blood flow velocity of the current frame.

In an embodiment of the present invention, the step of determining whether aliasing occurs further comprises comparing the blood flow energy of the previous frame with an energy threshold value and comparing the absolute value of the difference between the output blood flow velocity of the previous frame and the input blood flow velocity of the current frame with a velocity difference threshold value; and determining occurrence of aliasing to the output blood flow velocity of the previous frame, if the blood flow energy of the previous frame is larger than the energy threshold value and the absolute value of the difference between the output blood flow velocity of the previous frame and the input blood flow velocity of the current frame is larger than the velocity difference threshold value. The energy threshold value is related to human body part to be detected and the cut-off frequency of a wall filter, and the velocity difference threshold value is related to human body part to be detected, frame rate and the blood flow velocity scale during the detection.

The step of processing the input blood flow velocity of the current frame and the output blood flow velocity of the previous frame comprises: moving the output blood flow velocity of the previous frame to another position; and frame averaging the output blood flow velocity of the previous frame that has been moved and the input blood flow velocity of the current frame to obtain the output blood flow velocity of the current frame.

In an embodiment of the present invention, the another position is a no-aliasing position that is not limited by a pulse repetition frequency.

Preferably, the step of processing the input blood flow velocity of the current frame and the output blood flow velocity of the previous frame further comprises equalizing the output blood flow velocity of the current frame to a second threshold value if the output blood flow velocity of the current frame is larger than the second threshold value to prevent overflow.

Optionally, the step of moving the output blood flow velocity of the previous frame comprises determining a forward movement or a reverse movement based on the sign of the output blood flow velocity of the previous frame.

In an embodiment of the present invention, the output blood flow velocity of the current frame involved in the step of frame averaging is calculated according to:

$$V_{out}(n) = \text{sign}(V_{in}(n)) * [\alpha * |V'_{out}(n-1)| + (1-\alpha) * |V_{in}(n)|],$$

where, $V_{out}(n)$ is the output blood flow velocity of the current frame, sign(•) represents the sign of a variable in parentheses, α is a frame averaging coefficient, |•| represents an absolute value, $V'_{out}(n-1)$ refers to the blood flow velocity of the previous frame that has been moved, $V_{in}(n)$ refers to the input blood flow velocity of the current frame, $V'_{out}(n-1) = |V_{out}(n-1)| - \theta$, and θ represents movement amount.

The present invention further provides a device for color blood flow frame averaging. The device comprises: a velocity acquisition module for acquiring an input blood flow velocity of the current frame and an output blood flow velocity of the previous frame; a direction determination module for determining whether the input blood flow of the current frame is in an opposite direction to that of the output blood flow of the previous frame; an aliasing determination module for determining whether aliasing occurs to the output blood flow velocity of the previous frame if the input blood flow velocity of the current frame is in an opposite direction to that of the output blood flow velocity of the previous frame; and an aliasing processing module for processing the input blood flow velocity of the current frame and the output blood flow velocity of the previous frame to obtain an output blood flow velocity of the current frame if aliasing occurs to the output blood flow velocity of the previous frame.

The aliasing processing module comprises a velocity movement module for moving the output blood flow velocity of the previous frame to another position; and a frame averaging module for frame averaging the output blood flow velocity of the previous frame that has been moved and the input blood flow velocity of the current frame to obtain the output blood flow velocity of the current frame.

Preferably, the aliasing processing module further comprises an anti-overflow module for equalizing the output blood flow velocity of the current frame to a threshold value if the output blood flow velocity of the current frame is larger than the threshold value.

According to the existing technical scheme II, when the directions of the blood flow velocities of two consecutive frames are opposite to each other, the input blood flow velocity of the current frame is directly output upon color velocity frame averaging processing. In this case, since aliasing occurs to the blood flow velocity of the previous frame that takes part in the color frame averaging at some spatial distribution points, while it does not happen at other spatial distribution points, it will result in the presence of a flake-like "shadow" in the output blood flow velocity of the current frame upon color velocity frame averaging processing. The color frame averaging scheme according to the present invention can determine whether aliasing occurs to the output blood flow velocity of the previous frame based on the blood flow energy of the previous frame and the difference between the output blood flow velocity of the previous frame and the input blood flow velocity of the current frame. If aliasing occurrence is determined, the output blood flow velocity of the previous frame will be moved, and the output blood flow velocity of the previous frame that has been moved is subjected to the frame averaging. Whereby, the present invention can improve and eliminate the "shadow" in the output blood flow velocity of the current frame due to velocity aliasing of the previous frame existing in the prior color frame averaging processing, such that the velocity image having been subjected to blood flow frame averaging appears more natural and has a more reasonable distribution, and the image can be displayed more smoothly.

BRIEF DESCRIPTION OF THE DRAWINGS

The present invention will become more apparent from the following description of specific embodiments with reference to the drawings:

FIG. 3 shows blood flows of two consecutive frames, in which, FIG. 3a is a blood flow diagram of the previous frame, and FIG. 3b is a blood flow diagram of the current frame;

FIG. 4 shows curves of changes in the blood flow velocity of the two consecutive scanned frames shown in FIG. 3, in which, FIG. 4a shows a curve of changes in the blood flow velocity with time in area A, and FIG. 4b shows a curve of changes in the blood flow velocity with time in area B;

FIG. 5 shows a blood flow velocity of the current frame resultant from using an existing color frame averaging technology, in which, FIG. 5a shows a curve of changes in the blood flow velocity with time in area A, and FIG. 5b shows a curve of changes in the blood flow velocity with time in area B;

FIG. 8 shows a velocity profile after the aliased velocity has been moved, among which, FIG. 8a shows a curve of changes in the blood flow velocity with time in area A, and FIG. 8b shows the curve of changes in the blood flow velocity with time in area B;

DETAILED DESCRIPTION OF THE INVENTION

Figure 7:
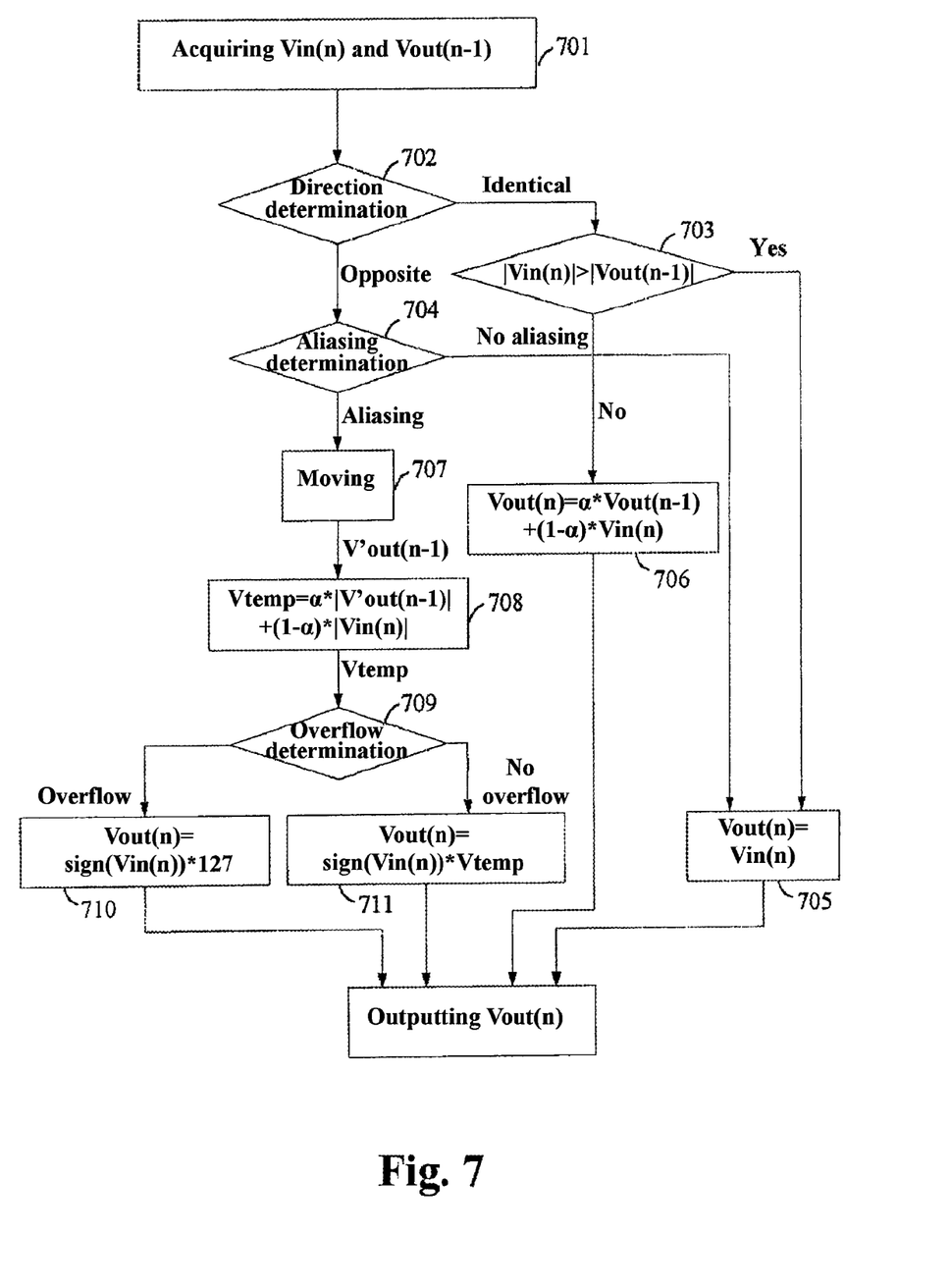
FIG. 7 is a flowchart of a method for color blood flow frame averaging according to the present invention.

In the present invention, there is provided a method for color blood flow frame averaging. The method for color blood flow frame averaging according to the present invention will be described in greater details hereunder in conjunction with the flowchart as shown in FIG. 7.

The input blood flow velocity $V_{in}(n)$ of the current frame and the output blood flow velocity $V_{out}(n-1)$ of the previous frame are acquired in step 701. The direction of the input blood flow velocity $V_{in}(n)$ of the current frame and the direction of the output blood flow velocity $V_{out}(n-1)$ of the previous frame are observed in the subsequent step 702. If the directions are identical, it goes to step 703, or otherwise goes to step 704.

In step 703, the input blood flow velocity $V_{in}(n)$ of the current frame is compared with the output blood flow velocity $V_{out}(n-1)$ of the previous frame. Preferably, the absolute value of the input blood flow velocity $|V_{in}(n)|$ of the current frame is compared with the absolute value of the output blood flow velocity $|V_{out}(n-1)|$ of the previous frame. If $|V_{in}(n)|$ is larger than $|V_{out}(n-1)|$, it goes to step 705. In step 705, the input blood flow velocity $V_{in}(n)$ of the current frame is outputted as the output blood flow velocity $V_{out}(n)$ of the current frame. Otherwise, it goes to step 706, in which, the input blood flow velocity $V_{in}(n)$ of the current frame and the output blood flow velocity $V_{out}(n-1)$ of the previous frame are frame-averaged, i.e., $V_{out}(n)=\alpha*V_{out}(n-1)+(1-\alpha)*V_{in}(n)$, where $\alpha$ is the frame averaging coefficient.

Obviously, the above frame averaging processing applies when the directions of the blood flow velocities of two consecutive frames are identical to each other. If the input blood flow velocity value of the current frame is larger than the output blood flow velocity value of the previous frame, the input blood flow velocity value of the current frame is directly outputted, such that an increase of the blood flow velocity can be swiftly shown on the display, thus increasing the pulsation of the blood flow velocity image. If the input blood flow velocity value of the current frame is lower than the output blood flow velocity value of the previous frame, the output velocity of the previous frame and the calculated velocity of the current frame are frame-averaged, and the resultant frame-averaged velocity is outputted as the output blood flow velocity of the current frame, thus increasing the sensitivity of the blood flow detection due to accumulation of frame averaging.

In step 704, it is decided whether aliasing occurs to the output blood flow velocity of the previous frame. In one embodiment of the present invention, the decision is made mainly based on two conditions. One is the blood flow energy corresponding to the blood flow velocity at each spatial point in the previous frame. If aliasing occurs to a certain spatial point in the blood flow, its corresponding blood flow energy is the maximum energy in the whole cardiac cycle. If the blood flow energy at a spatial point is large enough, it is likely that velocity is aliased at that point. The other condition is the difference between the blood flow velocity of the previous frame and the blood flow velocity of the current frame. Under the same velocity measurement condition, the larger the velocity difference, the more likely aliasing occurs to the blood flow velocity of the previous frame. Therefore, step 704 is implemented by comparing the blood flow energy $W_{out}(n-1)$ of the previous frame with an energy threshold value $W_{thr}$, and comparing the absolute value of the difference $|V_{out}(n-1)-V_{in}(n)|$ between the output blood flow velocity of the previous frame and the input blood flow velocity of the current frame with a velocity difference threshold value $V_{thr}$. If the blood flow energy $W_{out}(n-1)$ of the previous frame is larger than the energy threshold value $W_{thr}$, and in the mean time if the absolute value of the difference $|V_{out}(n-1)-V_{in}(n)|$ is larger than the threshold value $V_{thr}$, it is determined that aliasing occurs to the output blood flow velocity of the previous frame, and then step 707 starts. Otherwise, it is determined that aliasing does not occur, and step 705 starts instead. These steps will be described in greater details hereinafter. A person skilled in the art may readily understand that the determination on the occurrence of aliasing to the output blood flow velocity of the previous frame may depend on either one of the blood flow velocity, the blood flow energy, or the blood flow variance, or the combination of any two or three of the above three parameters.

In step 707, an anti-aliasing movement is performed on the output blood flow velocity of the previous frame, i.e., the output blood flow velocity $V_{out}(n-1)$ of the previous frame is moved to another position that is not limited by a pulse repetition frequency. In an embodiment of the present invention as shown in FIG. 8a, the velocity movement amount depends on the absolute value of the blood flow velocity, therefore, the velocity movement may be calculated as follows:

$$V'_{out}(n-1)=|V_{out}(n-1)|-\theta,$$

where, $\theta$ is the movement amount. In an embodiment of the present invention, $\theta$ is 256. Notably, it should be determined whether the movement is a forward movement or a reverse movement based on the sign of the output blood flow velocity of the previous frame. In the subsequent step 708, the absolute value of the output blood flow velocity $V'_{out}(n-1)$ of the previous frame that has been moved and the absolute value of the input blood flow velocity $V_{in}(n)$ of the current frame are frame-averaged, and the frame-averaged result gives an intermediate result variable $V_{temp}$.

When both the frame averaging coefficient $\alpha$ and the input blood flow velocity $V_{in}(n)$ of the current frame have a relatively large value, the intermediate result variable $V_{temp}$ may be larger than a threshold value. If the intermediate result variable $V_{temp}$ is outputted at this time as the output blood flow velocity of the current frame, overflow occurs. Therefore, an overflow determination step 709 is preferred according to one embodiment of the present invention. In step 709, the intermediate result variable $V_{temp}$ is compared with a threshold value. In an embodiment of the invention, the threshold value is equal to 127. If the intermediate result variable $V_{temp}$ is larger than the threshold value, it goes to step 710, where an anti-overflow processing is performed on the intermediate result variable $V_{temp}$, i.e., the intermediate result variable $V_{temp}$ is made equal to the threshold value, and the threshold value is outputted as the output blood flow velocity value of the current frame. Otherwise, it goes to step 711 where the intermediate result variable $V_{temp}$ is outputted as the output blood flow velocity value of the current frame. Notably, the direction of the output blood flow velocity of the current frame should be kept consistent with that of the input blood flow velocity of the current frame, which is implemented by multiplying the output blood flow velocity value of the current frame by the sign of the input blood flow velocity of the current frame.

As described above, if the output blood flow energy value of the previous frame is relatively low, or the difference between the output blood flow velocity of the previous frame and the input blood flow velocity of the current frame does not meet the conditions specific to the corresponding velocity level, aliasing does not occur to the output blood flow velocity of the previous frame. At this time, step 705 is performed. The input blood flow velocity $V_{in}(n)$ of the current frame is outputted as the output blood flow velocity of the current frame in step 705. This is commonly found in hepatic veins and thigh aorta. For hepatic veins, in a cardiac cycle, the blood flow goes away from liver at most of the times. However, there is always a reverse flow in hepatic veins for a very short period of time in each cardiac cycle. For the thigh aorta itself, the forward and reverse blood flows are alternately flowing.

Figure 8:
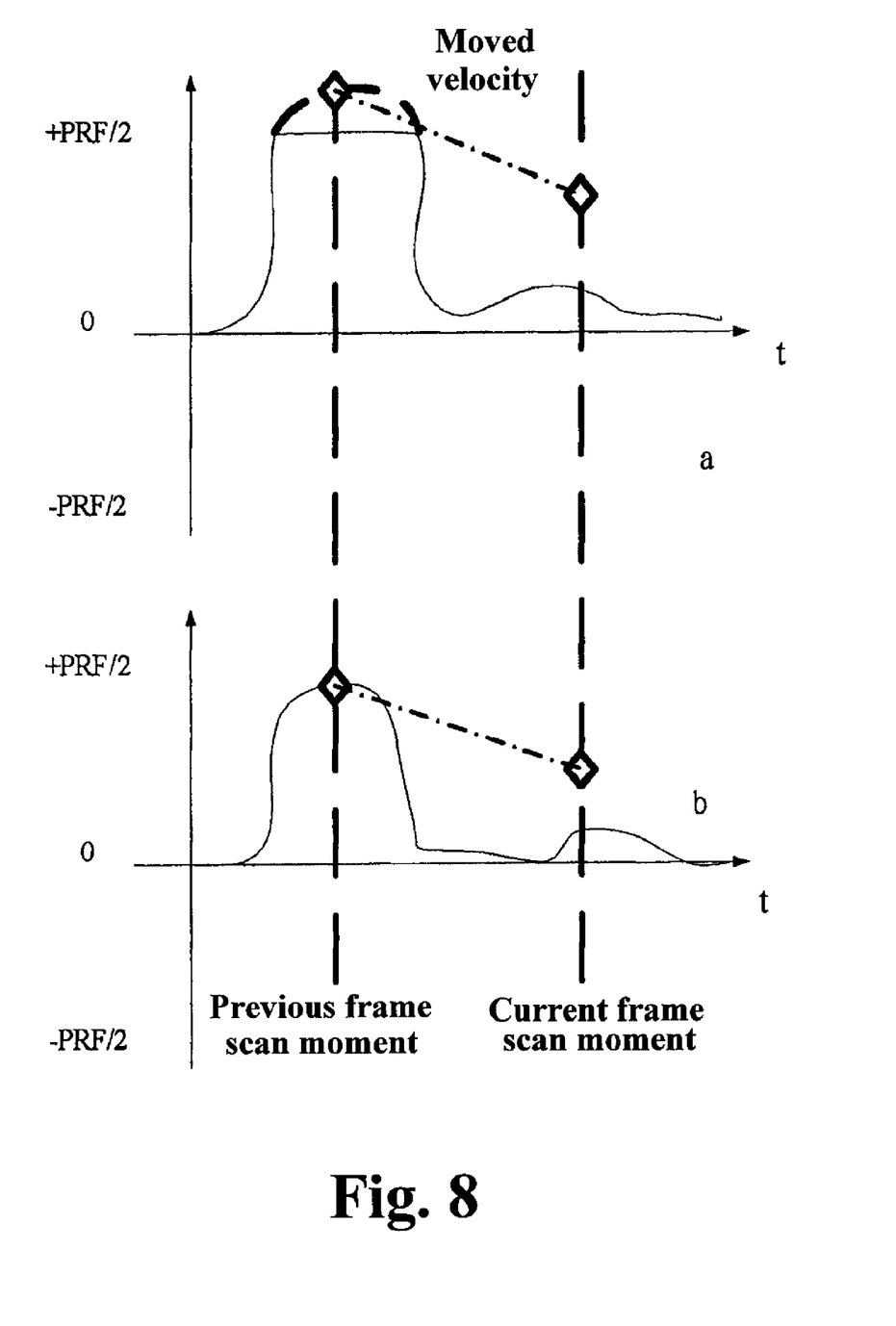

FIG. 8 shows a resultant velocity having been subjected to the color blood flow frame averaging according to the present invention. According to FIG. 8, the aliased velocity gets moved as indicated in area A. It is the velocity value after being moved (larger than 127) that is subjected to the frame averaging processing. The output blood flow velocity value (the position indicated by the diamond in FIG. 8a) of the current frame after the frame averaging processing is more reasonable compared to the blood flow velocity value (the position indicated by the diamond in FIG. 5a) of the current frame calculated using the existing technique described in scheme II. For the velocity frame averaging in the area B, as the direction of the blood flow velocity remains unchanged, the output velocity value of the current frame as shown in FIG. 8b is consistent with the output velocity value of the current frame as shown in FIG. 5b.

Figure 9:
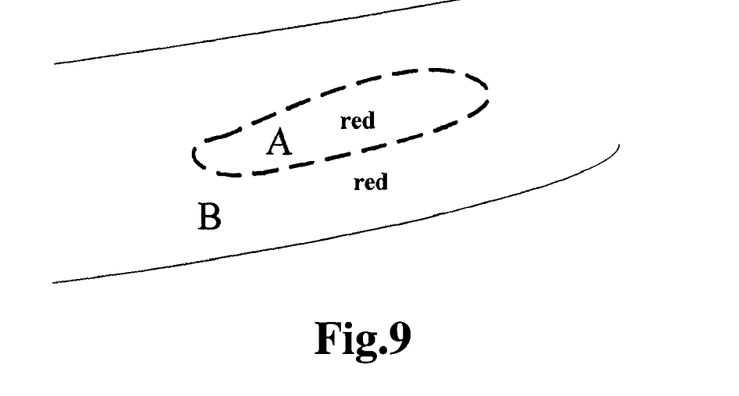
FIG. 9 is a blood flow velocity resultant from using the velocity frame averaging processing scheme according to the present invention.

FIG. 9 shows a velocity output after the color blood flow frame averaging processing according to the present invention. Since the output blood flow velocity of the previous frame in area A is determined aliased and moved to the expected position and then subjected to the frame averaging processing, the output blood flow velocity of the current frame in the area A should exhibit red instead of dark red after frame averaging, and should be of a larger value than the blood flow velocity in the area B. This is consistent with the characteristics of the clinic test. Hence, the velocity "shadow" accompanied with the existing frame averaging processing is eliminated, and furthermore the line trail along the edges intersecting the dark red area A and the red area B is removed such that the blood flow velocity appears more natural and has a more reasonable distribution.

Figure 10:
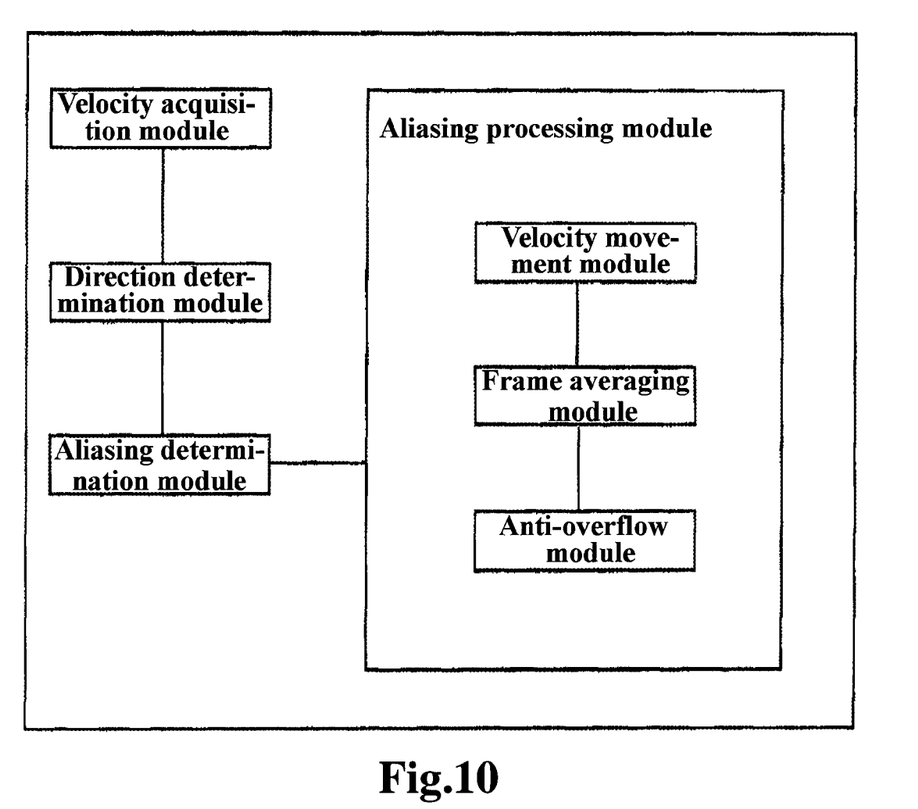
FIG. 10 is a block diagram of a device for color blood flow frame averaging according to the present invention.

The present invention further provides a device for color blood flow frame averaging, as shown in FIG. 10, which will be described in details as follows.

As shown in FIG. 10, the device for color blood flow frame averaging according to the present invention comprises a velocity acquisition module, a direction determination module, an aliasing determination module and an aliasing processing module. The aliasing processing module comprises a velocity movement module and a frame averaging module. In an embodiment of the present invention, the aliasing processing module further comprises an anti-overflow module. The operations of various modules will be described in details below.

Firstly, the velocity acquisition module acquires the input blood flow velocity of the current frame and the output blood flow velocity of the previous frame. Then, a direction determination module determines whether the direction of the input blood flow velocity of the current frame is identical to that of the output blood flow velocity of the previous frame. If not, the aliasing determination module determines whether aliasing occurs to the output blood flow velocity of the previous frame. The criterion for making such a determination is already described above, and thus is not additionally described herein.

If the aliasing determination module makes sure of the aliasing to the output blood flow velocity of the previous frame, the aliasing processing module gets into operations. Firstly, the velocity movement module moves the output blood flow velocity of the previous frame to a no-aliasing position that is not limited by the pulse repetition frequency. Compared to the existing technical solution, the output blood flow velocity of the previous frame that has been moved is further subjected to inter-frame velocity averaging processing performed by the frame averaging module. A person skilled in the art may readily understand that the frame averaging module may be implemented by a first-order recursive IIR filter, or a first-order FIR filter, or a high-order IIR or FIR filter. If the frame-averaged velocity exceeds an allowable maximum velocity value corresponding to PRF/2 under a correct detection, the anti-overflow module replaces the frame-averaged velocity with the allowable maximum velocity value.

If the direction of the blood flow velocity of the previous frame under the color blood flow frame averaging processing is opposite to that of the blood flow velocity of the current frame, but the conditions for determining aliasing are not satisfied, the aliasing determination module outputs the input blood flow velocity of the current frame to the system, thus avoiding a misjudgment of the presence of reverse blood flows in different time phases within one cardiac cycle that does exist in the human body.

The present invention has been applied to a commercial color ultrasonic apparatus. The present invention removes the unfavorable "shadow" occurring to the color blood flow velocity image as the result of the velocity aliasing, such that the image looks more natural, the blood flow velocity is more reasonably distributed and the image is displayed more smoothly.

Although the invention has been described above with reference to specific embodiments, it is not intended that the invention be limited to the above-mentioned embodiments. Various modifications and alternations may be made to the present invention without departing from the scope of the present invention. The scope of the present invention is defined by the appended claims. The words "first" and "second" as used in the description and the claims of the present invention are merely illustrative and should not be considered restrictive in any way.

REFERENCES

[1] D. D. Franklin, J. E. Powers, "ultrasonic flow velocity imaging systems with velocity image persistence", U.S. Pat. No. 5,215,094, 1993, ATL

[2] R. J. Collaris, A P G Hoeks, "postprocessing of velocity distributions in real time ultrasonic color velocity imaging", ultrasonics imaging, 16.249-264, 1994

[3] S. F. Forestieri, R. S. Spratt "temporal filtering of color Doppler signal data" U.S. Pat. No. 5,357,580, 1994, Diasonics

[4] J. A. Smith, M. Ellis, et.al., "color adaptive frame averaging", U.S. Pat. No. 5,467,770, 1995, GE

[5] T. Wong, Z. Banjanin, "persistence for ultrasonic flow imaging", U.S. Pat. No. 5,897,502, 1999, Siemens

What is claimed is:

1. A method for color blood flow frame averaging performed by an ultrasonic apparatus, comprising the steps of:
   acquiring an input blood flow velocity of a current frame and an output blood flow velocity of a previous frame;
   determining whether the input blood flow velocity of the current frame is in an opposite direction to that of the output blood flow velocity of the previous frame;
   determining whether aliasing occurs to the output blood flow velocity of the previous frame if the input blood flow velocity of the current frame is in an opposite direction to that of the output blood flow velocity of the previous frame; and
   processing the input blood flow velocity of the current frame and the output blood flow velocity of the previous frame to obtain an output blood flow velocity of the current frame if aliasing occurs to the output blood flow velocity of the previous frame, wherein the parameters regarding the previous frame comprise any one of or any combination of: a blood flow velocity of the previous frame, blood flow energy of the previous frame, a blood flow variance of the previous frame, and an absolute value of a difference between the output blood flow velocity of the previous frame and the input blood flow velocity of the current frame.

2. The method for color blood flow frame averaging of claim 1, wherein determining whether aliasing occurs further comprises: comparing parameters regarding the previous frame with corresponding first threshold values, and if the parameters regarding the previous frame are larger than the corresponding first threshold values, determining occurrence of aliasing to the output blood flow velocity of the previous frame.

3. The method for color blood flow frame averaging of claim 2, wherein determining whether aliasing occurs further comprises comparing the blood flow energy of the previous frame with an energy threshold value and comparing the absolute value of the difference between the output blood flow velocity of the previous frame and the input blood flow velocity of the current frame with a velocity difference threshold value; and determining occurrence of aliasing to the output blood flow velocity of the previous frame, if the blood flow energy of the previous frame is larger than the energy threshold value and the absolute value of the difference between the output blood flow velocity of the previous frame and the input blood flow velocity of the current frame is larger than the velocity difference threshold value.

4. The method for color blood flow frame averaging of claim 3, wherein the energy threshold value is related to human body part to be detected and the cut-off frequency of a wall filter, and the velocity difference threshold value is related to human body part to be detected, frame rate and the blood flow velocity scale during the detection.

5. The method for color blood flow frame averaging of claim 1, wherein processing the input blood flow velocity of the current frame and the output blood flow velocity of the previous frame comprises the steps of:
   moving the output blood flow velocity of the previous frame to another position; and
   frame averaging the output blood flow velocity of the previous frame that has been moved and the input blood flow velocity of the current frame to obtain the output blood flow velocity of the current frame.

6. The method for color blood flow frame averaging of claim 5, wherein the another position is a no-aliasing position that is not limited by a pulse repetition frequency.

7. The method for color blood flow frame averaging of claim 6, wherein moving the output blood flow velocity of the previous frame comprises determining a forward movement or a reverse movement based on the sign of the output blood flow velocity of the previous frame.

8. The method for color blood flow frame averaging of claim 7, wherein the output blood flow velocity of the current frame involved in the step of frame averaging is calculated according to:

$$V_{out}(n) = \text{sign}(V_{in}(n)) * [\alpha * |V'_{out}(n-1)| + (1-\alpha) * |V_{in}(n)|],$$

where, $V_{out}(n)$ is the output blood flow velocity of the current frame, sign(•) represents the sign of a variable in parentheses, $\alpha$ is a frame averaging coefficient, |•| represents an absolute value, $V'_{out}(n-1)$ refers to the blood flow velocity of the previous frame that has been moved, $V_{in}(n)$ refers to the input blood flow velocity of the current frame, $V'_{out}(n-1) = |V_{out}(n-1)| - \theta$, and $\theta$ represents movement amount.

9. The method for color blood flow frame averaging of claim 8, wherein $\theta$ is equal to 256.

10. The method for color blood flow frame averaging of claim 5, wherein processing the input blood flow velocity of the current frame and the output blood flow velocity of the previous frame further comprises the step of:
    equalizing the output blood flow velocity of the current frame to a second threshold value if the output blood flow velocity of the current frame is larger than the second threshold value to prevent overflow.

11. The method for color blood flow frame averaging of claim 10, wherein the second threshold value is an allowable maximum velocity value under a correct detection.

12. The method for color blood flow frame averaging of claim 11, wherein the allowable maximum velocity value is equal to 127.

13. A device for color blood flow frame averaging, comprising:
    a velocity acquisition module for acquiring an input blood flow velocity of a current frame and an output blood flow velocity of a previous frame;
    a direction determination module for determining whether the input blood flow velocity of the current frame is in an opposite direction to that of the output blood flow velocity of the previous frame;
    an aliasing determination module for determining whether aliasing occurs to the output blood flow velocity of the previous frame if the input blood flow velocity of the current frame is in an opposite direction to that of the output blood flow velocity of the previous frame; and
    an aliasing processing module for processing the input blood flow velocity of the current frame and the output blood flow velocity of the previous frame to obtain an output blood flow velocity of the current frame if aliasing occurs to the output blood flow velocity of the previous frame, wherein the aliasing processing module further comprises:
    an anti-overflow module for equalizing the output blood flow velocity of the current frame to a threshold value if the output blood flow velocity of the current frame is larger than the threshold value.

14. The device for color blood flow frame averaging of claim 13, wherein the aliasing processing module comprises:

a velocity movement module for moving the output blood flow velocity of the previous frame to another position; and a frame averaging module for frame averaging the output blood flow velocity of the previous frame that has been moved and the input blood flow velocity of the current frame to obtain the output blood flow velocity of the current frame.

15. The device for color blood flow frame averaging of claim 14, wherein the frame averaging module is implemented by a first-order recursive IIR filter, a first-order FIR filter, a high-order IIR filter or a high-order FIR filter.

* * * * *